United States Patent [19]

Nishimura et al.

[11] Patent Number: 4,559,408

[45] Date of Patent: Dec. 17, 1985

[54] PROCESS FOR STABILIZING METHYLENEIMINE COMPOUND AND STABILIZED METHYLENEIMINE COMPOSITION

[75] Inventors: Toshiaki Nishimura, Kanagawa; Masahiro Kurokawa, Hiratsuka, both of Japan

[73] Assignee: Mitsubishi Gas Chemical Co., Inc., Tokyo, Japan

[21] Appl. No.: 688,653

[22] Filed: Jan. 3, 1985

[30] Foreign Application Priority Data

Jan. 6, 1984 [JP] Japan .................................. 59-583

[51] Int. Cl.$^4$ ............................................. C07C 85/26
[52] U.S. Cl. ............................................. 564/2; 564/5; 526/183
[58] Field of Search ................... 564/2, 248, 272, 275, 564/278, 5; 526/183

[56] References Cited

U.S. PATENT DOCUMENTS 2,615,919 10/1952 Biswell ..................... 564/5
2,729,679 1/1956 Anderson ..................... 564/278
3,321,479 5/1967 Eberhardt et al. ................... 260/268

FOREIGN PATENT DOCUMENTS 20740 5/1969 Japan ............................. 564/275

OTHER PUBLICATIONS

Journal of the American Chemical Society, vol. 104, No. 7, pp. 2081-2083 (1982).
Journal of the American Chemical Society, vol. 85, No. 14, pp. 2178-2180 (1963).

Primary Examiner—Charles F. Warren
Assistant Examiner—R. A. Picard
Attorney, Agent, or Firm—Armstrong, Nikaido, Marmelstein & Kubovcik

[57] ABSTRACT

A cyclohexylmethyleneimine compound represented by the following general formula:

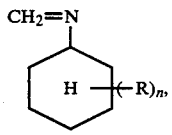

wherein R is an alkyl group bonded to individual carbon atom of the cyclohexyl ring and n is an integer of 0 to 5, or a methyleneimine composition containing at least the cyclohexylmethyleneimine compound can be stabilized by an organic lithium compound represented by the following general formula:

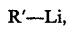

wherein R' is an alkyl, aryl or aralkyl group, and can be preserved stably for a long time.

17 Claims, No Drawings

PROCESS FOR STABILIZING METHYLENEIMINE COMPOUND AND STABILIZED METHYLENEIMINE COMPOSITION

BACKGROUND OF THE INVENTION

This invention relates to a process for stabilizing methyleneimine compounds including a cyclohexyl methyleneimine compound as an essential component and to a stabilized methyleneimine composition.

Methyleneimine compounds are compounds having a methylene group at the tertiary nitrogen and can readily undergo polymerization reaction in the presence of a very small amount of atmospheric moisture to produce polymers. Owing to this property, they can be used as a new type of instantaneous adhesive, or as raw materials for other chemicals. The polymers of methyleneimine compounds can be used in various applications, for example, as a catalyst for various urethane foams, a curing agent and a curing promoter for epoxy resin, a paint stabilizer, a curing agent and a vulcanization promoter for rubber latex, an electrode-protecting agent, a rust-proof agent, an electroconductive polymer obtained by quaternarizing the tertiary nitrogen in the polymer, an ion exchange resin, a polymeric coagulant, etc., and furthermore can be used as raw materials for synthesis of other chemicals by virtue of the reactivity of the tertiary amino group.

On the other hand, it is very difficult to preserve them stably for a long time owing to their reactivities, and no process for preserving them stably for a long time has been so far known.

As a result of extensive studies, the present inventors have unexpectedly found that a cyclohyxylmethyleneimine compound can be stabilized by the presence of an organic lithium compound, and other methyleneimine compounds alone are not stabilized by the presence of the organic lithium compound, but when they contain the cyclohexylmethyleneimine compound, they can be stabilized by the presence of the organic lithium compound, and have established the present invention.

SUMMARY OF THE INVENTION

An object of the present invention is to provide a process for stabilizing a cyclohexylmethyleneimine compound represented by the following general formula:

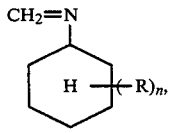

wherein R is an alkyl group bonded to individual carbon atom of the cyclohexyl ring and n is an integer of 0 to 5, characterized by adding thereto an organic lithium compound represented by the following general formula:

R'—Li, wherein R' is an alkyl, aryl or aralkyl group.

Another object of the present invention is to provide a process for stabilizing methyleneimine compounds containing a cyclohexylmethyleneimine compound represented by the following general formula as an essential component:

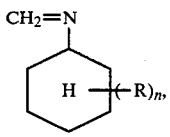

wherein R is an alkyl group bonded to individual carbon atom of the cyclohexyl ring and n is an integer of 0 to 5, chracterized by adding thereto an organic lithium compound represented by the following general formula:

R'—Li, wherein R' is an alkyl, aryl or aralkyl group.

Another object of the present invention is to provide a stabilized methyleneimine composition which comprises at least a cyclohexylmethyleneimine compound represented by the following general formula:

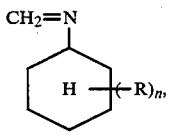

wherein R is an alkyl group bonded to individual carbon atom of the cyclohexyl ring and n is an integer of 0 to 5 and an organic lithium compound represented by the following general formula:

R'—Li, wherein R' is an alkyl, aryl or aralkyl group, as essential components.

As R in the formula, the alkyl group includes, for example, methyl, ethyl, propyl, butyl, etc., and the typical cyclohexylmethyleneimine compounds are, for example, cyclohexylmethyleneimine, 2- or 4-methylcyclohexylmethyleneimine, 2,3-, 2,4-, 2,5-, 2,6-, 3,4- or 3,5-dimethylcyclohexylmethyleneimine, 2- or 4-ethylcyclohexylmethyleneimine, 2,3-diethylcyclohexylmethyleneimine, 2- or 4-propylcyclohexylmethyleneimine, 2,3-dipropylcyclohexylmethyleneimine, 2- or 4-butylcyclohexylmethyleneimine, 2,3-dibutylcyclohexylmethyleneimine, etc.

The methyleneimine compounds that can be stabilized in their mixtures with the cyclohexylmethyleneimine compound, are, for example, benzylmethyleneimine, 3-methylbenzylmethyleneimine, hexylmethyleneimine, heptylmethyleneimine, octylmethyleneimine, etc. These methyleneimine compounds alone are not stabilized by the presence of an organic lithium compound, but can be stabilized thereby, so long as they contain even a very small amount of a cyclohexylmethyleneimine compound. In that case it is preferable to contain at least 0.05% by weight of the cyclohexylmethyleneimine compound on the basis of total methyleneimine. The upper limit of the cyclohexylmethyleneimine content is not particularly limited, and the stabilization effect can be obtained with various cyclohexylmethyleneimine content, but when the cyclohexylmethyleneimine compound is added to the other methyleneimine compound merely as a stabilizer together with the organic lithium compound, it is satisfactory to add thereto not more than 5% by weight of the cyclohexylmethyleneimine compound.

The organic lithium compounds for use in the present invention are compounds represented by the following general formula:

R'—Li wherein R' is an alkyl, aryl or aralkyl group, that is, compounds in which such an alkyl group as ethyl, butyl, etc., such an aryl group as phenyl, naphthyl, etc., or such an aralkyl group as benzyl, etc. is bonded to lithium, and include, for example, butyl lithium, phenyl lithium, benzyl lithium, etc. Particularly preferable is butyl lithium.

These organic lithium compounds ignite, when brought in contact with oxygen, and thus are usably preserved as dissolved in hexane, ether, etc. They can be used in the solution state.

1 to 1,000 ppm, particularly preferably 10 to 500 ppm, of the organic lithium compound is used on the basis of the weight of the methyleneimine compounds containing the cyclohexylmethyleneimine compound as an essential component. Too much addition of the organic lithium compound has no special effect and thus has no special significance, and rather lowers the purity of methyleneimine compounds containing the cyclohexylmethyleneimine compound as an essential component.

The methyleneimine compounds containing the cyclohexylmethyleneimine compound as an essential component can be stably preserved for a long time by adding the organic lithium compound thereto. When the methyleneimine compounds are used in the said applications, usually it is not particularly necessary to remove the organic lithium compound therefrom though dependent on the applications.

PREFERRED EMBODIMENTS OF THE INVENTION

The present invention will be described in detail below, referring to Examples and Comparative Examples.

EXAMPLE 1

Added to 50 g of cyclohexylmethyleneimine was 0.1 g of a 15 wt.% n-butyl lithium solution in hexane, which corresponded to 300 ppm of n-butyl lithium on the basis of the weight of cyclohexylmethyleneimine, and the mixture was placed in a sealed container. The container was left standing in a thermostat at 0° C.

It was found that the mixture was stable even after 120 days.

EXAMPLE 2

Added to 50 g of cyclohexylmethylimine was 0.1 g of a 5 wt.% n-butyl lithium solution in hexane, which corresponded to 100 ppm of n-butyl lithium on the basis of the weight of cyclohexylmethyleneimine, and the mixture was placed in a sealed container. The container was left standing in a thermostat at 0° C.

It was found that the mixture was stable even after 90 days.

EXAMPLE 3

Added to 50 g of 4-methylcyclohexylmethyleneimine was 0.2 g of a 2 wt.% n-butyl lithium solution in hexane, which corresponded to 80 ppm of n-butyl lithium on the basis of the weight of 4-methylcyclohexylmethyleneimine. The mixture was placed in a sealed container, and the container was left standing in a thermostat at 0° C.

It was found that the mixture was stable even after 90 days.

EXAMPLE 4

Added to 50 g of cyclohexylmethyleneimine was 0.6 g of a 3.8 wt.% phenyl lithium solution in cyclohexane/diethyl ether (70/30 by weight), which corresponded to 456 ppm of phenyl lithium on the basis of the weight of cyclohexylmethyleneimine. The mixture was placed in a sealed container and the container was left standing in a thermostat at 0° C.

It was found that the mixture was stable even after 60 days.

EXAMPLE 5

10 g of cyclohexylmethyleneimine and 40 g of benzylmethyleneimine were mixed together, and 0.2 g of a 5 wt.% n-butyl lithium solution in hexane was added to the methyleneimine mixture, where the amount of n-butyl lithium corresponded to 200 ppm on the basis of the weight of the methyleneimine mixture. The resulting mixture was placed in a sealed container, and the container was left standing in a thermostat at 0° C.

It was found that the mixture was stable even after 120 days.

EXAMPLE 6

25 g of cyclohexylmethyleneimine and 25 g of 3-methylbenzylmethyleneimine were mixed together, and 0.6 g of a 3.8 wt.% phenyl lithium solution in cyclohexane/diethyl ether (70/30 by weight) was added to the methyleneimine mixture, where the amount of phenyl lithium corresponded to 456 ppm on the weight of the methyleneimine mixture. The resulting mixture was placed in a sealed container, and the container was left standing in a thermostat at 0° C.

It was found that the mixture was stable even after 60 days.

EXAMPLE 7

1 g of cyclohexylmethyleneimine and 19 g of benzylmethyleneimine were mixed together, and 0.9 g of a 1 wt.% n-butyl lithium solution in hexane was added to the methyleneimine mixture, where the amount of n-butyl lithium corresponded to 450 ppm on the basis of the weight of the methyleneimine mixture. The resulting mixture was placed in a sealed container, and the container was left standing in a thermostat at 0° C.

It was found that the mixture was stable even after 150 days.

EXAMPLE 8

Added to 100 g of benzylmethyleneimine was a mixture of 0.5 g of cyclohexylmethyleneimine and 3.0 g of a 1 wt.% n-butyl lithium solution in hexane, where the amount of n-butyl lithium corresponded to 300 ppm on the basis of the weight of total methyleneimines. The resulting mixture was placed in a sealed container, and the container was left standing in a thermostat at 0° C.

It was found that the mixture was stable even after 120 days.

EXAMPLE 9

Added to 50 g of benzylmethyleneimine was a mixture of 0.15 g of cyclohexylmethyleneimine and 1.1 g of a 1 wt.% n-butyl lithium solution in hexane, where the amount of n-butyl lithium corresponded to 220 ppm on the basis of the weight of total methyleneimines. The resulting mixture was placed in a sealed container, and the container was left standing in a thermostat at 0° C.

It was found that the mixture was stable even after 100 days.

COMPARATIVE EXAMPLE 1

50 g of cyclohexylmethyleneimine was placed in the same sealed container as in Example 1, and preserved at 0° C. It was found that cyclohexylmethyleneimine was completely changed into polymers after 30 hours.

COMPARATIVE EXAMPLE 2

50 g of 4-methylcyclohexylmethyleneimine was placed in the same sealed container as in Example 1, and preserved at 0° C. It was found that 4-methylcyclohexylmethyleneimine was completely changed into polymers after 30 hours.

What is claimed is:

1. A process for stabilizing a cyclohexylmethyleneimine compound represented by the following general formula:

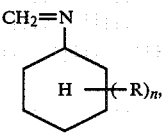

wherein R is an alkyl group bonded to individual carbon atom of the cyclohexyl ring and n is an integer of 0 to 5, which comprises adding thereto an organic lithium compound represented by the following general formula:

wherein R' is an alkyl, aryl or aralkyl group.

2. A process for stabilizing methyleneimine compounds containing a cyclohexylmethyleneimine compound represented by the following general formula as an essential component:

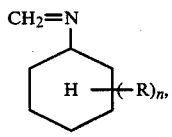

wherein R is an alkyl group bonded to individual carbon atom of the cyclohexyl ring and n is an integer of 0 to 5, which comprises adding thereto an organic lithium compound represented by the following general formula:

wherein R' is an alkyl, aryl or aralkyl group.

3. A process according to claim 1 or 2, wherein the alkyl group as R is methyl, ethyl, propyl or butyl.

4. A process according to claim 1 or 2, wherein the cyclohexylmethyleneimine compound is cyclohexylmethyleneimine, 2- or 4-methylcyclohexylmethyleneimine, 2,3-, 2,4-, 2,5-, 2,6-, 3,4- or 3,5-dimethylcyclohexylmethyleneimine, 2- or 4-ethylcyclohexylmethyleneimine, 2,3-diethylcyclohexylmethyleneimine, 2- or 4-propylcyclohexylmethyleneimine, 2,3-dipropylcyclohexylmethyleneimine, 2- or 4-butylcyclohexylmethyleneimine, or 2,3-dibutylcyclohexylmethyleneimine.

5. A process according to claim 2, wherein the methyleneimine compound that can be stabilized with the cyclohexylmethyleneimine compound is benzylmethyleneimine, 3-methylbenzylmethyleneimine, hexylmethyleneimine, heptylmethyleneimine, or octylmethyleneimine.

6. A process according to claim 2, wherein at least 0.05% by weight of the cyclohexylmethyleneimine compound is contained on the basis of total methyleneimine.

7. A process according to claim 1 or 2, wherein the R' for the organic lithium compound is ethyl, butyl, phenyl, naphthyl, or benzyl.

8. A process according to claim 1 or 2, wherein the organic lithium compound is butyl lithium, phenyl lithium or benzyl lithium.

9. A process according to claim 1 or 2, wherein 1 to 1000 ppm of the organic lithium compound is added on the basis of the weight of total methyleneimine compounds.

10. A stabilized methyleneimine composition which comprises at least a cyclohexylmethyleneimine compound represented by the following general formula:

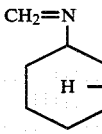

wherein R is an alkyl group bonded to individual carbon atom of the cyclohexyl ring and n is an integer of 0 to 5 and an organic lithium compound represented by the following general formula:

wherein R' is an alkyl, aryl or aralkyl group, as essential components.

11. A stabilized methyleneimine composition according to claim 10, wherein the alkyl group as R is methyl, ethyl, propyl or butyl.

12. A stabilized methyleneimine composition according to claim 10, wherein the cyclohexylmethyleneimine compound is cyclohexylmethyleneimine, 2- or 4-methylcyclohexylmethyleneimine, 2,3-, 2,4-, 2,5-, 2,6-, 3,4- or 3,5-dimethylcyclohexylmethyleneimine, 2- or 4-ethylcyclohexylmethyleneimine, 2,3-diethylcyclohexylmethyleneimine, 2- or 4-propylcyclohexylmethyleneimine, 2,3-dipropylcyclohexylmethyleneimine, 2- or 4-butylcyclohexylmethyleneimine, or 2,3-dibutylcyclohexylmethyleneimine.

13. A stabilized methyleneimine composition according to claim 10, wherein at least 0.05% by weight of the cyclohexylmethyleneimine compound is contained, when other methyleneimine compound than the cyclohexylmethyleneimine compound is contained, on the basis of total methyleneimines.

14. A stabilized methyleneimine composition according to claim 13, wherein other methyleneimine compound is benzylmethyleneimine, 3-methylbenzylmethyleneimine hexylmethyleneimine, heptylmethyleneimine or octylmethyleneimine.

15. A stabilized methyleneimine composition according to claim 10, wherein the R' for the organic lithium compound is ethyl, butyl, phenyl, naphthyl, or benzyl.

16. A stabilized methyleneimine composition according to claim 10, wherein the organic lithium compound is butyl lithium, phenyl lithium or benzyl lithium.

17. A stabilized methyleneimine composition according to claim 10, wherein 1 to 1,000 ppm of the organic lithium compound is contained or the basis of the weight of the methyleneimine compound.

* * * * *